(12) United States Patent
Noelle et al.

(10) Patent No.: US 8,465,740 B2
(45) Date of Patent: Jun. 18, 2013

(54) REGULATORY T CELL MEDIATOR PROTEINS AND USES THEREOF

(75) Inventors: Randolph J. Noelle, Plainfield, NH (US); Li-Fan Lu, Seattle, WA (US); Sergio Quezada, New York, NY (US); David Gondek, Brookline, MA (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 13/326,792

(22) Filed: Dec. 15, 2011

(65) Prior Publication Data

US 2012/0195894 A1 Aug. 2, 2012

Related U.S. Application Data

(62) Division of application No. 11/912,397, filed as application No. PCT/US2006/015239 on Apr. 24, 2006, now Pat. No. 8,236,304.

(60) Provisional application No. 60/674,567, filed on Apr. 25, 2005.

(51) Int. Cl.
*A61K 39/395* (2006.01)

(52) U.S. Cl.
USPC ...................................... 424/130.1

(58) Field of Classification Search
None
See application file for complete search history.

(56) References Cited

U.S. PATENT DOCUMENTS

| | | | |
|---|---|---|---|
| 6,924,355 B2 | 8/2005 | Baker et al. | |
| 2003/0054406 A1 | 3/2003 | Baker et al. | |
| 2008/0248007 A1 | 10/2008 | Chen | |
| 2011/0027278 A1 | 2/2011 | Noelle et al. | |

OTHER PUBLICATIONS

Duttagupta et al., Crit. Rev. Immunol., 2009, 29: 469-486.*
Tuladhar et al., Int. J. Biol. Sci., 2011, 7: 1382-1390.*
Blazar et al., J. Immunol., 1996, 157: 3250-3259.*
Lederman et al.; Molecular Immunology, 1991, 28: 1171-1181.*
Sequence alignment, 2012, 1 page.*
Di Maro et al., 1999; 208: 125-131.
Lederman et al., Molecular Immunology, 1991, 28: 1171-1181. Sequence Alignment, 2010, 1 page.
NCBI Accession No. NM_028732 [gi:31980769] with Revision History—Mar. 20, 2001-May 7, 2006. 143249860 which replaced 31980768 is provided.
NCBI Accession No. NP_080401 [gi:13385632] with Revision History—Mar. 20, 2001-May 7, 2006.
NCBI Accession No. NM_022153 [gi: 62339431] with Revision History—Apr. 7, 2005-Jun. 26, 2007.
NCBI Accession No. NP_071436 [gi: 62339431] with Revision History—Apr. 7, 2005-Aug. 13, 2006.
NCBI Accession No. NM_138530 [gi:51491892] with Revision History—Apr. 4, 2002-Nov. 18, 2006.
NCBI Accession No. AK004116 [gi:12835174] with Revision History—Feb. 8, 2011-Sep. 2, 2005.
NCBI Accession No. NM_026125 [gi:13385631] with Revision History—Mar. 20, 2001-May 7, 2006. 142365660 which replaced 13385631 is provided.
NCBI Accession No. BC089443 [gi:59807840] with Revision History—Feb. 15, 2005-Jun. 6, 2006.
NCBI Accession No. AAH89443 [gi:59807841] with Revision History—Feb. 15, 2005-Jun. 6, 2006.
NCBI Accession No. XI_233720 [gi:109475938] with Revision History—Jan. 13, 2003-Jun. 22, 2006.
GenBank Accession No. NP_083008 (Mar. 3, 3010) platelet receptor Gi24 isoform 1 precursor [Mus musculus].
GenBank Accession No. NP_071436 (Sep. 3, 2009), platelet receptor Gi24 precursor [*Homo spaiens*].
Nomi, T. et al., Clinical significance and therapeutic potential of the programmed death-1 ligand/programmed death-1 pathway in human pancreatic cancer. Clin. Cancer Res. 2007, vol. 13, pp. 2152-2157.
Wang, L. et al., VISTA, a novel mouse Ig superfamily ligand that negatively regulates T cell response. J. Exp. Med. Mar. 7, 2011, vol. 208. No. 3, pp. 577-592.

* cited by examiner

*Primary Examiner* — Ilia Ouspenski
(74) *Attorney, Agent, or Firm* — Hunton & Williams LLP

(57) ABSTRACT

The present invention relates to novel regulatory T cell proteins. One protein, designated PD-L3, resembles members of the PD-L1 family, and co-stimulates αCD3 proliferation of T cells in vitro. A second, TNF-like, protein has also been identified as being upregulated upon αCD3/αGITR stimulation. This protein has been designated $T^{reg}$-sTNF. Proteins, antibodies, activated T cells and methods for using the same are disclosed.

6 Claims, No Drawings

REGULATORY T CELL MEDIATOR PROTEINS AND USES THEREOF

INTRODUCTION RELATED APPLICATIONS

This application is a divisional of U.S. application Ser. No. 11/912,397 filed Jun. 4, 2008 now U.S. Pat. No. 8,236,304, which is U.S. National Stage (371) of PCT/2006/015239 filed Apr. 24, 2006, which claims benefit of U.S. Provisional Patent Application Ser. No. 60/674,567, filed Apr. 25, 2005, all of which are herein incorporated by reference in their entireties.

BACKGROUND OF THE INVENTION

Induction of an immune response requires T cell expansion, differentiation, contraction and establishment of T cell memory. T cells must encounter antigen presenting cells (APCs) and communicate via T cell receptor (TCR)/major histocompatibility complex (MHC) interactions on APCs. Once the TCR/MHC interaction is established, other sets of receptor-ligand contacts between the T cell and the APC are required, i.e. co-stimulation via CD154/CD40 and CD28/B7.1-B7.2. The synergy between these contacts is suggested to result, in vivo, in a productive immune response capable of clearing pathogens and tumors, and in some cases capable of inducing autoimmunity.

Another level of control has been identified, namely regulatory T cells ($T^{reg}$). This specific subset of T cells is generated in the thymus, delivered into the periphery, and is capable of constant and inducible control of T cells responses in vitro and in vivo (Sakaguchi (2000) Cell 101(5):455-8; Shevach (2000) Annu. Rev. Immunol. 18:423-49; Bluestone and Abbas (2003) Nat. Rev. Immunol. 3(3):253-7). $T^{reg}$ are represented by a $CD4^+CD25^+$ phenotype and also express high levels of cytotoxic T lymphocyte-associated antigen-4 (CTLA-4), OX-40, 4-1BB and the glucocorticoid inducible TNF receptor-associated protein (GITR) (McHugh, et al. (2002) Immunity 16(2):311-23; Shimizu, et al. (2002) Nat. Immun. 3(2):135-42). Elimination of $T^{reg}$ cells by 5 day neonatal thymectomy or antibody depletion using anti-CD25, results in the induction of autoimmune pathology and exacerbation of T cells responses to foreign and self-antigens, including heightened anti-tumor responses (Sakaguchi, et al. (1985) J. Exp. Med. 161(1):72-87; Sakaguchi, et al. (1995) J. Immunol. 155(3):1151-64; Jones, et al. (2002) Cancer Immun. 2:1). In addition, $T^{reg}$ have also been involved in the induction and maintenance of transplantation tolerance (Hara, et al. (2001) J. Immunol. 166(6):3789-3796; Wood and Sakaguchi (2003) Nat. Rev. Immunol. 3:199-210), since depletion of $T^{reg}$ with anti-CD25 monoclonal antibodies results in ablation of transplantation tolerance and rapid graft rejection (Jarvinen, et al. (2003) Transplantation 76:1375-9). Among the receptors expressed by $T^{reg}$, GITR seems to be an important component since in vitro or in vivo ligation of GITR on the surface of $T^{reg}$ with an agonistic monoclonal antibody results in rapid termination of $T^{reg}$ activity (McHugh, at al. (2002) supra; Shimizu, et al. (2002) supra), also resulting in autoimmune pathology (Shimizu, at al. (2002) supra) and ablation of transplantation tolerance.

DNA microarray analysis has been conducted with a population of $T^{reg}$ to identify genes differentially expressed by $T^{reg}$ (Gavin, et al. (2002) Nat. Immunol. 3(1):33-41; McHugh, at al. (2002) supra). The expression pattern of genes of $CD4^+CD25^-$ and $CD4^+CD25^+$ T cells was compared (Gavin, et al. (2002) supra) as was the expression pattern of these two populations of cells after activation by anti-CD3 antibody and IL-2 for 12 and 48 hours (McHugh, et al. (2002) supra). However, gene regulation by GITR signaling was not assessed.

T cell activation is dependent upon signs transferred through antigen-specific T cells receptor recognition and accessory receptors on the T cell. As the maintenance of immunologic peripheral homeostatis is regulated by co-stimulatory molecules, which play a critical role in suppressing autoreactive lymphocytes, identification of these co-stimulatory molecules is needed.

A novel T cell co-stimulatory molecule has now been identified and will be useful in modulating immune responses in autoimmunity, cancer, infectious disease and transplantation.

SUMMARY OF THE INVENTION

The present invention is a composition containing an isolated PD-L3 protein comprising the amino acid sequence set forth in SEQ ID NO:5 and a pharmaceutically acceptable carrier. In one embodiment, the PD-L3 protein is operably linked to a heterologous protein.

The present invention is also an expression vector harboring an isolated nucleic acid encoding PD-L3 protein comprising the amino acid sequence set forth in SEQ ID NO:5; and host cells containing said vector.

The present invention is also an isolated binding agent which specifically binds to a PD-L3 protein comprising the amino acid sequence set forth in SEQ ID NO:5.

The present invention is further a method for modulating an immune cell response by contacting an immune cell with a PD-L3 protein, or binding agent thereof, in the presence of a primary signal so that a response of the immune cell is modulated.

DETAILED DESCRIPTION OF THE INVENTION

A novel member of the PD-L1 family has now been identified in $T^{reg}$ cells. This novel protein has been designated PD-L3. Like other members of the PD-L1 family, PD-L3 co-stimulates αCD3 proliferation of T cells in vitro. In addition, the expression of PD-L3 is increased in αCD3 activated $T^{reg}$ and reduced in the presence of αGITR. A second, TNF-like, protein has also been identified as being upregulated upon αCD3/αGITR stimulation. This protein has been designated $T^{reg}$-sTNF. These proteins may be involved in contact-dependent and paracrine suppression of immunity and would therefore be useful for modulating (e.g., inhibiting or stimulating) an immune response and in the treatment of diseases and conditions involving $T^{reg}$ signaling.

PD-L3 and $T^{reg}$-sTNF were identified by global transcriptional profiling of resting $T^{reg}$, $T^{reg}$ activated with αCD3, and $T^{reg}$ activated with αCD3/αGITR. αGITR was selected for this analysis as triggering of GITR on $T^{reg}$ has been shown to extinguish their contact-dependent suppressive activity (Shimizu, et al. (2002) supra). PD-L3 and $T^{reg}$-sTNF were identified on AFFIMETRIX® DNA arrays based on their unique expression patterns (Table 1). PD-L3 exhibited an increase in expression in αCD3 activated $T^{reg}$ and reduced expression in the presence of αGITR; and $T^{reg}$-sTNF exhibited a αCD3/αGITR-dependent increase in expression.

TABLE 1

| mRNA | Relative Expression | | |
|---|---|---|---|
| | None | αCD3 | αCD3/αGITR |
| PD-L3 | 6 | 10 | 7 |
| T$^{reg}$-sTNF | 0.2 | 0.3 | 1.5 |

Purified CD4$^+$CD25$^+$ T cells were stimulated in culture overnight with none, αCD3, or αCD3/αGITR, and RNA isolated for real-time PCR analysis. Expression listed is relative to actin.

PD-L3 was cloned and sequenced and, as indicated, is a member of the PD-L1 family. This Ig family of co-stimulatory molecules is composed of positive regulatory co-receptors such as CD28 and ICOS, and also negative regulatory signals such as those mediated by CTLA-4, PD-1, and BTLA molecules. Knockout studies of negative co-stimulatory receptors have demonstrated the necessity of these receptors in controlling autoimmunity and establishing peripheral tolerance (Chen (2004) Nat. Rev. Immunol. 4:336-47). The receptors of the PD-L1 family are type I transmembrane proteins containing a single IgV domain while the ligands are type I transmembrane proteins having both an IgV and an IgC extracellular domain.

Sequence analysis revealed that PD-L3 corresponded to mouse locus Ricken ID 4632428N05 with an mRNA coding sequence given as GENBANK accession number NM_028732 and protein sequence give as NP_080401. The nucleic acid sequence encoding mouse PD-L3 is set forth herein as SEQ ID NO:1 and the mouse PD-L3 protein sequence is set forth as SEQ ID NO:2. PD-L3 has an Ig domain which shares 26.5% homology with that of PD-L1 (B7-H1). The mouse PD-L3 gene is located on chromosome 10 (62.2 Mb) and is composed of 6 exons, creating a transcript of 4799 bases in length and coding for a 309-residue type I transmembrane protein. Pfam and Interpro (Integrated resource of Protein Families, Domains and Sites) predict a signal sequence (positions 1-32) and an Ig-like domain (positions 47-147). The human homolog of PD-L3 is located on chromosome 10 (72.9 Mb) and composed of 6 exons thereby generating a transcript of 4689 bases in length coding for a 311 residue protein. The human homolog mRNA coding sequence is provided in GENBANK accession number NM_022153 and protein sequence give as NP_071436. The nucleic acid sequence encoding human PD-L3 is set forth herein as SEQ ID NO:3 and the human PD-L3 protein sequence is set forth as SEQ ID NO:4. Mouse and human genes share 74% homology and are 68% identical at the protein level. Homologs were also identified in Rattus norvegicus on chromosome 20 (27.7 Mb; GENBANK accession number BC098723), as well as Fugu rubripes and Danio rerio. In particular embodiments, PD-L3 proteins of the present share the common amino acid sequence set forth in SEQ ID NO:5.

A PD-L3-Ig fusion protein was produced according to standard methods, purified and titered into cultures of purified CD4$^+$ T cells, APC and αCD3. On day 3, all wells were pulsed with tritiated thymidine ($^3$H-TdR) and proliferation was determined. Like other PD-L1 proteins, PD-L3 was shown to co-stimulate αCD3 proliferation of T cells in vitro (Table 2).

TABLE 2

| Treatment | Proliferation (cpm/culture) |
|---|---|
| αCD3 (0.1 µg/mL) | 900 ± 600 |
| hIgG1 (10 µg/mL) | 600 ± 400 |
| PD-L3-Fc (0.5 µg/mL) | 2300 ± 1150 |
| PD-L3-Fc (1.0 µg/mL) | 3900 ± 900 |
| PD-L3-Fc (10 µg/mL) | 4200 ± 650 |

Using a rabbit anti-PD-L3 antibody, PD-L3 protein was localized to lymphoid organs and prominently found in brain tissue. Further, four transgenic mice were produced which expressed full-length PD-L3 under the control of the human elongation factor 1 promoter. These mice were generated using lentiviral vector pWPT. Similar to other PD-L1 family members (Appay, et al. (2002) J. Immunol. 168:5954-8), it is contemplated that PD-L3 will function as a negative regulator in vivo while functioning to co-stimulate αCD3 T cell proliferation in vitro.

The second co-stimulatory molecule identified, T$^{reg}$-sTNF, contains a TNF-like domain similar to those found in C1q family of proteins. Sequence analysis revealed that T$^{reg}$-sTNF corresponded with mouse locus Ricken ID 1110035L05 with an mRNA coding sequence given as GENBANK accession number NM_026125 and protein sequence give as NP_080401. The nucleic acid sequence encoding mouse T$^{reg}$-sTNF is set forth herein as SEQ ID NO:6 and the mouse T$^{reg}$-sTNF protein sequence is set forth herein as SEQ ID NO:7. This TNF-like molecule is located on chromosome 4 (154.1 Mb), near OX40 and GITR, and composed of 8 exons, creating a transcript 1301 bases in length coding for a 308 residue soluble protein. Pfam and Interpro protein predict a signal sequence (positions 1-19), a proline rich collagen triple helix-like motif (positions 99-111), and a TNF-like motif (positions 176-306). Collectively, these motifs are similar to those of the C1q family of proteins, although this TNF-like protein does not contain the characteristic C1q-like motif that identifies this family. The human homolog of T$^{reg}$-sTNF is located on chromosome 1 (1.1 Mb) and is composed of 7 exons thereby generating a transcript of 1014 bases in length coding for a 337 residue protein. The human coding sequence for the human homolog of T$^{reg}$-sTNF is provided as GENBANK accession number BC089443 and protein sequence give as AAH89443.1. The nucleic acid sequence encoding human T$^{reg}$-sTNF is set forth herein as SEQ ID NO:8 and the human T$^{reg}$-sTNF protein sequence is set forth as SEQ ID NO:9. Mouse and human genes share 65.3% homology and 66% identify at the protein level. Homologs were also identified in Rattus norvegicus on chromosome 5 (172.8 Mb; GENBANK accession number XM_233720.2), as well as Fugu rubripes and Danio rerio. In particular embodiments, T$^{reg}$-sTNF proteins of the present share the common amino acid sequence set forth in SEQ ID NO:10.

Having identified a novel immune cell regulatory molecule produced by T$^{reg}$ cells, the present invention relates to a PD-L3 protein, agents which bind PD-L3, nucleic acids encoding PD-L3 and methods of using PD-L3 and PD-L3 binding agents to modulate immune cell responses.

As used herein, a PD-L3 protein is intended to include a protein that has a sequence which is substantially similar to that of mouse PD-L3 (i.e., SEQ ID NO:2) or human PD-L3 (i.e., SEQ ID NO:4) and in particular embodiments has the consensus amino acid sequence set forth in SEQ ID NO:5. The term substantially similar refers to sequences having sequence variation (e.g., conservative substitutions and/or variations) that do not materially affect the nature of the protein (i.e., the structure, stability characteristics, substrate specificity and/or biological activity of the protein). In general, a protein having an amino acid sequence that is substantially similar to SEQ ID NO:2 or SEQ ID NO:4 has at least 70% identity to that of SEQ ID NO:2 or SEQ ID NO:4, over its entire length and exhibits at least one biological activity of PD-L3. The present invention further provides for a protein which has an amino acid sequence which shares at least 80% identity, at least 90% identity, at least 95% identity, or more desirably at least 97-99% identity, to that of SEQ ID NO:2 or SEQ ID NO:4 over the entire length of SEQ ID NO:2 or SEQ ID NO:4.

Percent identical and percent similar are used herein in comparisons among amino acid and nucleic acid sequences. When referring to amino acid sequences, identity or percent identical refers to the percent of the amino acids of the subject amino acid sequence that have been matched to identical amino acids in the compared amino acid sequence by a sequence analysis program. Percent similar refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are well-known in the art (see, e.g., Taylor (1986) *J. Theor. Biol. H* 9:205). When referring to nucleic acid molecules, percent identical refers to the percent of the nucleotides of the subject nucleic acid sequence that have been matched to identical nucleotides by a sequence analysis program.

Identity and similarity can be readily calculated by known methods. Nucleic acid sequences and amino acid sequences can be compared using computer programs that align the similar sequences of the nucleic or amino acids thus define the differences. Such methods include the BLAST programs (NCBI) and the DNAstar system (Madison, Wis.). However, equivalent alignments and similarity/identity assessments can be obtained through the use of any standard alignment software. For instance, the GCG Wisconsin Package, available from the Genetics Computer Group in Madison, Wis., can also be used to compare sequence identity and similarity.

A PD-L3 protein can be in the form of a mature protein (i.e. lacking a signal sequence, residues 1-32 of SEQ ID NO:1 or SEQ ID NO:2) or can be a part of a larger protein such as a fusion protein (e.g., fused to Fc). It is often advantageous to also include amino acid sequences which contain secretory or leader sequences, pro-sequences, sequences which aid in purification such as multiple histidine residues, or an additional sequence for stability during recombinant production. Accordingly, one embodiment of the present invention is a mature PD-L3 protein lacking N-terminal signal sequences. Another embodiment of the present invention is a fusion protein composed of PD-L3, or a fragment thereof, operably linked to a heterologous peptide or polypeptide (e.g., GST, Ig, His$_6$, and the like) such that the fused proteins are translated in-frame. As used herein, a heterologous peptide or protein is one which is not naturally found to be operably linked to PD-L3.

A particular suitable heterologous peptide is an immunoglobulin constant region, for example, a human Cγ1 domain or Cγ$_4$ domain (e.g., the hinge, CH2 and CH3 regions of human IgCγ1, or human IgCγ4; see e.g., Capon, et al. U.S. Pat. Nos. 5,116,964; 5,580,756; 5,844,095 and the like). Such constant regions may retain regions which mediate effector function (e.g., Fc receptor binding) or may be altered to reduce effector function.

Fragments of a PD-L3 protein are also included in the invention. A fragment is a protein having an amino acid sequence that is entirely the same as part, but not all, of the amino acid sequence of the aforementioned PD-L3 protein. Fragments include, for example, truncation polypeptides having the amino acid sequence of a PD-L3 protein, except for deletion of a continuous series of residues that includes the amino terminus, or a continuous series of residues that includes the carboxyl terminus or deletion of two continuous series of residues, one including the amino terminus and one including the carboxyl terminus. Other fragments are biologically active fragments. Biologically active fragments are those that mediate PD-L3 activity (e.g., co-stimulation of T cells or modulation of an immune response), including those with a similar activity or an improved activity, or with a decreased undesirable activity. Also included are those that are antigenic or immunogenic in an animal.

A PD-L3 protein of the invention can be prepared in any suitable manner. If produced in situ, the protein can be purified from appropriate sources, e.g., appropriate vertebrate cells e.g., mammalian cells for instance T$^{reg}$ cells from human, mouse, bovine or rat.

Alternatively, the availability of nucleic acid molecules encoding the PD-L3 protein enables production of PD-L3 using in vitro expression methods known in the art. For example, a cDNA or gene can be cloned into an appropriate in vitro transcription vector, for in vitro transcription, followed by cell-free translation in a suitable cell-free translation system. In vitro transcription and translation systems are commercially available, e.g., from PROMEGA® Biotech, Madison, Wis., or GIBCO-BRL®, Rockville, Md. In vitro transcription and translation is suitable for preparing small amounts of native or mutant proteins for research purposes, particularly since it allows the incorporation of radioactive nucleotides.

Larger quantities of PD-L3 protein can be produced by expression in a suitable prokaryotic or eukaryotic system. For example, part or all of a DNA molecule, such as the coding portion of SEQ ID NO:1 or SEQ ID NO:3 can be inserted into a plasmid vector adapted for expression in a bacterial cell (such as *Escherichia coli*) or a yeast cell (such as *Saccharomyces cerevisiae*), or into a baculovirus vector for expression in an insect cell. Such vectors contain the regulatory elements necessary for expression of the DNA in the host cell, positioned in such a manner as to permit expression of the DNA into mRNA and mRNA into protein in the host cell. Such regulatory elements required for expression include promoter sequences, transcription initiation sequences and, optionally, enhancer sequences. Suitable vectors for recombinant protein expression in mammalian, yeast, or prokaryotic systems are commercially available from such sources as STRATAGENE®, INVITROGEN™, Pharmacia and the like.

Host-specific secretion signals can be used to facilitate purification of the resulting protein. The coding sequence for the secretion peptide is operably linked to the 5' end of the coding sequence for the protein, and this hybrid nucleic acid molecule is inserted into a plasmid adapted to express the protein in the host cell of choice. Plasmids specifically designed to express and secrete foreign proteins are available from commercial sources. For example, if expression and secretion is desired in *E. Coli*, commonly used plasmids include pTrcPPA (Pharmacia); pPROK-C and pKK233-2 (CLONTECH™); and pNH8a, pNH16a, pcDNAII and pAX (STRATAGENE®), among others.

A PD-L3 protein produced by in vitro transcription and translation or by gene expression in a recombinant prokaryotic or eukaryotic system can be purified according to methods known in the art (e.g., fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; or gel filtration using, for example, SEPHADEX® G-75).

Alternatively, a synthetic PD-L3 protein can be prepared using various synthetic methods of peptide synthesis via condensation of one or more amino acid residues, in accordance with conventional peptide synthesis methods. For example, peptides are synthesized according to standard solid-phase methodologies, such as may be performed on an APPLIED BIOSYSTEMS™ Model 430A peptide synthesizer (APPLIED BIOSYSTEMS™, Foster City, Calif.), according to manufacturer's instructions. Other methods of synthesizing peptides or peptidomimetics, either by solid phase methodologies or in liquid phase, are well-known to those skilled in the art.

PD-L3 peptidomimetics (Fauchere, J. (1986) Adv. Drug Res. 15:29; Veber and Freidinger (1985) TINS p. 392; and Evans et al. (1987) J. Med. Chem. 30:1229) are also contemplated. Peptidomimetics are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), such as human PD-L3, but have one or more peptide linkages optionally replaced by a linkage such as —$CH_2NH$—, —$CH_2S$—, —$CH_2$—$CH_2$—, —CH=CH— (cis and trans), —$COCH_2$—, —CH(OH)$CH_2$—, and —$CH_2SO$—, by methods known in the art (see, e.g., Spatola (1983) In: Chemistry and Biochemistry of Amino Acids, Peptides, and Proteins, Weinstein, B., ed., Marcel Dekker, New York, p. 267; Morley (1980) Trends Pharm. Sci. pp. 463-468; Hudson, et al. (1979) Int. J. Pept. Prot. Res. 14:177-185); Spatola, et al. (1986) Life Sci. 38:1243-1249; Hann (1982) J. Chem. Soc. Perkin Trans. I. 307-314; Jennings-White, et al. (1982) Tetrahedron Lett. 23:2533; Holladay, et al. (1983) Tetrahedron Lett. (1983) 24:4401-4404; Hruby (1982) Life Sci. (1982) 31:189-199).

Whether recombinantly-produced or chemically-synthesized, PD-L3 (including PD-L3 fusion proteins or biologically active PD-L3 fragments) can be formulated into a pharmaceutically acceptable composition for use in accordance with the methods disclosed herein. A PD-L3 protein is generally formulated with a pharmaceutically acceptable carrier, such as buffered saline; a polyol (e.g., glycerol, propylene glycol, liquid polyethylene glycol and the like); carbohydrates such as glucose, mannose, sucrose or dextrans, mannitol; amino acids such as glycine; antioxidants; chelating agents such as EDTA or glutathione; preservatives or suitable mixtures thereof. In addition, a pharmaceutically acceptable carrier can include any solvent, dispersion medium, and the like which may be appropriate for a desired route of administration of the composition. The use of such carriers for pharmaceutically active substances is known in the art. Suitable carriers and their formulation are described, for example, in Remington: The Science and Practice of Pharmacy, Alfonso R. Gennaro, editor, 20th ed. Lippingcott Williams & Wilkins: Philadelphia, Pa., 2000.

A PD-L3 protein of the present invention can be used to identify binding partners of PD-L3, i.e., binding agents and receptors. In these assays, PD-L3 is allowed to form a physical interaction with the unknown binding partner(s), often in a heterologous solution of molecules. The binding complex is then isolated, and the identity of the binding partner is determined (e.g., via mass spec or sequence analysis). Alternatively, a panel of rational binding partners (e.g., CTLA-4, PD-1, or BTLA) can be screened with a PD-L3 protein. These procedures are greatly facilitated by simple methods for isolating PD-L3 protein, e.g., precipitation using immunologically-specific antibodies to the PD-L3 protein, or purification with PD-L3 protein bound to a solid support. In one embodiment, a PD-L3 protein is attached to a solid support via a covalent linkage. In other embodiments, attachment is via a non-covalent linkage, for example, between members of a high affinity binding pair (e.g., ligand/receptor or antigen/antibody pairs). Suitable solid supports include beads, e.g., magnetized beads or beads which are dense enough to be separated form non-associated protein by centrifugation. Alternatively, the PD-L3 protein can be used in a yeast two hybrid system such as the Ga14/LacZ system (see Clark, et al. (1998) Proc. Natl. Acad. Sci. USA 95:5401-5406) to identify binding partners.

A PD-L3 protein of the present invention can also be used as a regulatory signal in a method for modulating, i.e., stimulating or inhibiting, an immune cell response. The prototypic immune response described herein is stimulation of T cells ($CD4^+$), but one of ordinary skill in the art will readily appreciate that the method can be applied to modulation of other T cell-mediated and/or B cell-mediated immune responses that are influenced by modulation of T cell co-stimulation. By way of example, immune responses of tumor-reactive lymphocytes ($CD8^+$; Hellström, et al. (2001) Proc. Natl. Acad. Sci. USA 98:6783-6788), $CD43^+$ T cells (Wang, et al. (2004) J. Immunol. 173(10):6294-302), and natural killer cells can be modulated. In addition, immune responses that are indirectly effected by T cell activation, e.g., antibody production (humoral responses) and activation of cytokine responsive cells, e.g., macrophages are also contemplated.

In one embodiment, a PD-L3 protein is used as a co-stimulatory signal for stimulating or enhancing immune cell activation. A co-stimulatory signal, as used herein, refers to a signal, which in combination with a primary signal, such as TCR/CD3 ligation, leads to immune cell activation. The co-stimulatory signal can be used simultaneously with or subsequent to the primary signal to achieve the desired result. The term activation, within the context of T cells, refers to the induction of cellular proliferation. Activation of a T cell may also induce cytokine production and performance of regulatory or cytolytic effector functions. T cell activation preferably results in at least a 2.5- to 4.5-fold increase in the cell population as compared to cells which have not been co-stimulated (i.e., no stimulation or stimulated with a primary signal only). T cell activation can be quantitated as exemplified herein via tritiated thymidine incorporation or by analyzing cytokine production. Cytokines can be measured according to biological activity or protein accumulation (e.g., as determined by various immuno-based, activity, or other assays). Alternatively, mRNA production can be measured to establish levels of stimulation of transcription. In particular embodiments, the primary and co-stimulatory signals are further used in combination with other agents, such as cytokines (IL-2, IL-4, IL-7, IL-10, IL-12, etc.) or antigen presenting cells, for optimal activation.

In another embodiment, a PD-L3 protein is used as an inhibitory signal for inhibiting or decreasing immune cell activation. In this embodiment, the inhibitory signal binds to an inhibitory receptor (e.g., CTLA4 or PD-1) on an immune cell thereby antagonizing the primary signal which binds to an activating receptor (e.g., via a TCR, CD3, BCR, or Fc polypeptide). Inhibition includes, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

In particular embodiments, the primary signal is a ligand (e.g., CD3 or anti-CD3) that binds TCR and initiates a primary stimulation signal. Such TCR ligands are readily available from commercial sources and specific examples include anti-CD3 antibody OKT3, prepared from hybridoma cells obtained from the American Type Culture Collection, and anti-CD3 monoclonal antibody G19-4. In an alternative embodiment, a primary signal is delivered to a T cell through other mechanisms including a protein kinase C activator, such as a phorbol ester (e.g., phorbol myristate acetate), and a calcium ionophore (e.g., ionomycin, which raises cytoplasmic calcium concentrations), or the like. The use of such agents bypasses the TCR/CD3 complex but delivers a stimulatory signal to T cells. Other agents acting as primary signals can include natural and synthetic ligands. A natural ligand can include MHC with or without a peptide presented. Other ligands can include, but are not limited to, a peptide, polypeptide, growth factor, cytokine, chemokine, glycopeptide, soluble receptor, steroid, hormone, mitogen, such as PHA, or other superantigens, peptide-MHC tetramers (Altman, et al. (1996) *Science* 274(5284):94-6) and soluble MHC dimers (Dal Porto, et al (1993) Proc. Natl. Acad. Sci. USA 90: 6671-5).

Immune cells activated in accordance with the method of the instant invention can subsequently be expanded ex vivo and used in the treatment and prevention of a variety of diseases; e.g., human T cells which have been cloned and expanded in vitro maintain their regulatory activity (Groux, et al. (1997) *Nature* 389(6652):737-42). Prior to expansion, a source of T cells is obtained from a subject (e.g., a mammals such as a human, dog, cat, mouse, rat, or transgenic species thereof). T cells can be obtained from a number of sources, including peripheral blood mononuclear cells, bone marrow, lymph node tissue, cord blood, thymus tissue, tissue from a site of infection, spleen tissue, tumors or T cell lines. T cells can be obtained from a unit of blood collected from a subject using any number of techniques known to the skilled artisan, such as FICOLL™ separation.

Alternatively, T cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis are washed to remove the plasma fraction and to place the cells in an appropriate buffer (e.g., phosphate buffered saline (PBS) or wash solution lacking calcium or other divalent cations) or media for subsequent processing steps. After washing, the cells are resuspended in a variety of biocompatible buffers, such as, calcium-free, magnesium-free PBS.

Isolation of T cells from peripheral blood lymphocytes can be carried out by lysing the red blood cells and depleting the monocytes, for example, by centrifugation through a PERCOLL™ gradient. A specific subpopulation of T cells, such as $CD28^+$, $CD4^+$, $CD8^+$, $CD45RA^+$, and $CD45RO^+$ T cells, can be further isolated by positive or negative selection techniques well-known to the skilled. Enrichment of a T cell population by negative selection can be accomplished with a combination of antibodies directed to surface markers unique to the negatively selected cells. For example, to enrich for $CD4^+$ cells by negative selection, a monoclonal antibody cocktail typically includes antibodies to CD14, CD20, CD11b, CD16, HLA-DR, and CD8.

T cells for stimulation can also be frozen after isolation. Many freezing solutions and parameters are known in the art and will be useful in this context. One method involves suspending the cells in PBS containing 20% DMSO and 8% human serum albumin, or other suitable cell freezing media, and subsequently freezing the cells at −80° C. at a rate of 1° C. per minute and stored in the vapor phase of a liquid nitrogen storage tank. Other methods of controlled freezing can be used as well as uncontrolled freezing immediately at −20° C. or in liquid nitrogen.

Those of ordinary skill in the art will readily appreciate that stimulation and expansion of T cells described herein can be carried out in a variety of environments (i.e., containers). For example, such containers can be culture flasks, culture bags, or any container capable of holding cells (e.g., a bioreactor), preferably in a sterile environment. For example, several manufacturers currently make devices that can be used to grow cells and be used in combination with the methods of the present invention. See for example, Celdyne Corp. (Houston, Tex.), Unisyn Technologies (Hopkinton, Mass.), Synthecon, Inc. (Houston, Tex.), Aastrom Biosciences, Inc. (Ann Arbor, Mich.), Wave Biotech LLC (Bedminster, N.J.). Further, patents covering bioreactors include U.S. Pat. Nos. 6,096,532; 5,985,653; 5,888,807; and 5,190,878.

The present invention also relates to a vector, in particular an expression vector, containing nucleic acids encoding a PD-L3 protein for therapeutic use and production of recombinant PD-L3 protein. A PD-L3 nucleic acid of the present invention includes nucleic acids encoding the PD-L3 protein containing the amino acid sequence set forth in SEQ ID NO:5 and fragments, and nucleic acids substantially similar thereto. More specifically, PD-L3 nucleic acids of the invention include nucleic acids encoding mouse and human PD-L3 protein, wherein such nucleic acids are set forth in SEQ ID NO:1 and SEQ ID NO:3, respectively. A nucleic acid that is substantially similar to a PD-L3 nucleic acid shares at least 70% identity over its entire length with a nucleotide sequence encoding a PD-L3 protein of SEQ ID NO:2 or SEQ ID NO:4, and a nucleic acid having a nucleotide sequence that is at least 70% identical to that of SEQ ID NO: 1 or SEQ ID NO:3, over its entire length. In particular embodiments, a nucleic acid that is substantially similar to a PD-L3 nucleic acid shares at least 80% identity, at least 90% identity, at least 95% identity, or more desirably at least 97-99% identity, to that of SEQ ID NO:1 or SEQ ID NO:3 over the entire length of SEQ ID NO:1 or SEQ ID NO:3. Also encompassed within the scope of a PD-L3 nucleic acid is a nucleotide sequence which has sufficient identity to a nucleotide sequence contained in SEQ ID NO:1 or SEQ ID NO:3, to hybridize under conditions useable for amplification, as a probe or marker, or antisense or siRNA.

In accordance with the present invention, nucleic acids having the appropriate level sequence homology (i.e., 70% identity or greater) with part or all the coding regions of SEQ ID NO:1 or SEQ ID NO:3 can be identified by using hybridization and washing conditions of appropriate stringency. For example, hybridizations can be performed, according to the method of Sambrook, et al. ((1989) *Molecular Cloning, a Laboratory Manual*, Cold Spring Harbor Laboratories, New York) using a hybridization solution containing 1.0% SDS, up to 50% formamide, 5×SSC (150 mM NaCl, 15 mM trisodium citrate), 0.05% sodium pyrophosphate (pH 7.6), 5×Denhardt's solution, and 100 microgram/mL denatured, sheared salmon sperm DNA. Hybridization is carried out at 37-42° C. for at least six hours. Following hybridization, filters are washed as follows: 5 minutes at room temperature in 2×SSC and 1% SDS; 15 minutes at room temperature in 2×SSC and 0.1% SDS; 30 minutes to 1 hour at 37° C. in 2×SSC and 0.1% SDS; and 2 hours at 45-55° C. in 2×SSC and 0.1% SDS, changing the solution every 30 minutes.

One common formula for calculating the stringency conditions required to achieve hybridization between nucleic acid molecules of a specified percent identity is set forth by: $T_m$=81.5° C.+16.6 log 10 ([Na+]/(1.0+0.7[Na+]))+0.7% GC-500/size (Wetmur (1991) *Crit. Rev. Biochem. Mol. Biol.* 26:227-259)

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the of the hybrid. Wash conditions should be as stringent as possible for the degree of identity of the probe for the target. In regards to the nucleic acids of the present invention, a moderate stringency hybridization is defined as hybridization in 6×SSC, 5×Denhardt's solution, 0.5% SDS and 100 μg/mL denatured salmon sperm DNA at 42° C., and wash in 2×SSC and 0.5% SDS at 55° C. for 15 minutes. A high stringency hybridization is defined as hybridization in 6×SSC, 5×Denhardt's solution, 0.5% SDS and 100 μg/mL denatured salmon sperm DNA at 42° C., and wash in 1×SSC and 0.5% SDS at 6-5° C. for 15 minutes. Very high stringency hybridization is defined as hybridization in 6×SSC, 5×Denhardt's solution, 0.5% SDS and 100 μg/mL denatured salmon sperm DNA at 42° C., and wash in 0.1×. SSC and 0.5% SDS at 65° C. for 15 minutes.

Oligonucleotides (sense or antisense strands of DNA, cDNA or RNA) having sequences capable of hybridizing with at least one sequence of a nucleic acid molecule encoding the PD-L3 protein are useful as probes for detecting PD-L3 genes or transcripts and can also be useful in the treatment of various diseases or conditions, when delivered by an appropriate vehicle to the affected cells. Oligonucleotides for use as probes, primers, antisense, or siRNA are based on rationally-selected nucleic acid sequences chosen from SEQ ID NO:1 or SEQ ID NO:3. Such oligonucleotides can be used for the detection and isolation of nucleic acids encoding PD-L3 or inhibition of PD-L3 expression. Further, amino acid sequences of SEQ ID NO:2 and SEQ ID NO:4 can be used to design degenerate oligonucleotide primers, as is commonly done by those skilled in the art, for screening cDNA libraries from, e.g., bovine, canine, and feline to obtain PD-L3 homologs from bovine, canine, and feline, respectively.

The nucleotide sequences encoding the PD-L3 protein of SEQ ID NO:2 or SEQ ID NO:4 can be identical to the protein encoding sequence contained in SEQ ID NO:1 or SEQ ID NO:3, or can be a sequence, which as a result of the redundancy (degeneracy) of the genetic code, also encodes the protein of SEQ ID NO:2 or SEQ ID NO:4.

When the nucleic acids of the invention are used for the recombinant production of a PD-L3 protein, the nucleic acid can include the coding sequence for the mature protein or a fragment thereof, by itself; the coding sequence for the mature protein or fragment in reading frame with other coding sequences, such as those encoding a leader or secretory sequence, or other fusion peptide or protein as discussed supra. For example, a marker sequence which facilitates purification of the fused polypeptide can be encoded. The PD-L3 nucleic acid can also contain non-coding 5' and 3' sequences, such as transcribed, non-translated sequences, splicing and polyadenylation signals, ribosome binding sites and sequences that stabilize mRNA.

Nucleic acids of the present invention can be maintained as DNA in any convenient cloning vector, e.g., in plasmid cloning/expression vector, such as pBLUESCRIPT® (STRATAGENE®), that is propagated in a suitable *E. coli* host cell. As described above, PD-L3 nucleic acids may be used to produce large quantities of substantially pure PD-L3 proteins, or selected fragments thereof.

Hence, the present invention also relates to vectors, in particular expression vectors, that contain a PD-L3 nucleic acid, and isolated host cells that are genetically engineered with said vectors. Expression vectors harboring PD-L3 nucleic acids are discussed supra and generally contain all the necessary regulatory sequences, for example, promoter and terminator sequences, operably linked to the PD-L3 nucleic acids such that the PD-L3 coding sequence is transcribed into RNA and subsequently translated into protein or in the case of antisense, transcribed into RNA. Large numbers of suitable vectors and regulatory sequences are known to those of skill in the art, and are commercially available. The following vectors are provided by way of example, bacterial vectors pQE70, pQE60, pQE-9 (QIAGEN®), pBS, pD10, pBLUESCRIPT° SK, pBSKS, pNH8A, pNHI8A, $pNH_{46}A$ (STRATAGENE®) and pRIT5 (Pharmacia); and eukaryotic vectors pWLNEO, pSV2CAT, pOG44, pXTI, pSG (STRATAGENE®) pSVK3, pBPV, pMSG, pSVL (Pharmacia). As further examples, a PD-L3 cDNA of can be inserted in the pEF/myc/cyto vector (INVITROGEN™) or the pCMV-Tag3b vector (STRATAGENE®) and transformed (e.g., calcium phosphate transfection, DEAE-dextran mediated transfection, microinjection, cationic lipid-mediated transfection, electroporation) into Hela thereby facilitating purification and use of PD-L3.

However, any other plasmid or vector can be used as long as they are replicable and viable in the host. In addition, a complete mammalian transcription unit and a selectable marker can be inserted into a prokaryotic plasmid for use in in vivo procedures. The resulting vector is then amplified in bacteria before being transfected into cultured mammalian cells or delivered directly to the subject with an acceptable carrier. Examples of vectors of this type include pTK2, pHyg and pRSVneo. Hence, these plasmids, constructs and vectors can be used in both in vivo and ex vivo procedures. Ex vivo procedures involve the removal of a host cell (e.g., a $T^{reg}$ cell) from a subject, recombinant manipulation of the cell (i.e., transformation, transduction or transfection with a suitable PD-L3 expression vector), and the re-delivery of the cell back into its host environment.

Representative examples of appropriate hosts for in vitro procedures include bacterial cells, such as streptococci, staphylococci, *E. coli, Streptomyces* and *Bacillus subtilis* cells; fungal cells, such as yeast cells and *Aspergillus* cells, insect cells such as *Drosophila* S2 and *Spodoptera* Sf9 cells; animal cells such as CHO, COS, HeLa, 0127, 3T3, BHK, and HEK 293 cells, and plant cells. The selection of an appropriate host is deemed to be within the scope of those skilled in the art from the teachings herein.

Genetic material, such as the nucleic acids of the present invention, can be delivered to cells, in vivo, using various different plasmid-based delivery platforms, including but not limited to recombinant ADV (such as that described in U.S. Pat. No. 6,069,134), AAV (such as those described by U.S. Pat. No. 5,139,941), MMLV, Herpes Simplex Virus (U.S. Pat. No. 5,288,641), cytomegalovirus, lentiviral, and overall, retroviral gene delivery systems, well-known and practiced with in the art.

Techniques for preparing replication defective, infective viruses are well-known in the art (see, e.g., Gluzman et al. (1982) *Virology* 123(1):78-92). These systems typically include a plasmid vector including a promoter sequence (e.g., CMV immediate early, HSV thymidine kinase, early and late SV40, LTRs from retrovirus, and mouse metallothionein-1) operably linked to the nucleotide coding the gene of interest (inserted into an appropriate gene insertion site, i.e., an IRES site), as well as a terminating signal (such as a poly-A tail, i.e., BGH), and the appropriate mutations so as to make the delivery vehicle replication defective (e.g., Psi sequence deletions) and safe for therapeutic uses. The construction of the appropriate elements in a vector system containing the nucleotides of the present invention is well within the skills of one versed in the recombinant arts.

Therapeutic nucleic acids can be delivered to target cells via basic transfection methods such as permeabilizing the cell membrane physically or chemically. Liposomes or protein conjugates formed with certain lipids and amphophilic peptides can also be used for transfection (Stewart, et al. (1992) *Hum. Gene Ther.* 3(3):267-75; Zhu, et al. (1993) *Science* 261(5118):209-11). This approach is particularly effective in ex vivo procedures involving leukocytes, which can be temporarily removed from the body and can tolerate the cytotoxicity of the treatment.

A second, transduction approach, capitalizes on the natural ability of viruses to enter cells, bringing their own genetic material with them. For example, retroviruses can integrate their genes into the host genome, transferring a large amount of foreign genetic material, infecting a broad spectrum of species and cell types and of being packaged in special cell-lines (Miller (1992) *Curr. Top. Microbiol. Immunol.* 158:1-24).

A third method uses other viruses, such as adenovirus, herpes simplex viruses (HSV), cytomegalovirus (CMV), and adeno-associated virus (AAV), which are engineered to serve as vectors for gene transfer. For example, in an adenovirus gene transfer systems recombinant engineered adenovirus is rendered replication-incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 Kb of foreign DNA and can be grown to high titers in 293 cells with persistent expression of transgenes following adenoviral infection in vivo.

In addition to therapeutic uses and recombinant protein production, vectors and host cells disclosed herein are useful for producing transgenic animals which constitutively over-express PD-L3 or are deficient in PD-L3 protein production (i.e., knock out animals).

The present invention further relates to an isolated binding agent which specifically recognizes and binds to a PD-L3 protein. Binding agents are intended to include antibodies as well as peptide aptamers.

Peptide aptamers which specifically bind to a PD-L3 protein can be rationally designed or screened for in a library of aptamers (e.g., provided by Aptanomics SA, Lyon, France). In general, peptide aptamers are synthetic recognition molecules whose design is based on the structure of antibodies. Peptide aptamers consist of a variable peptide loop attached at both ends to a protein scaffold. This double structural constraint greatly increases the binding affinity of the peptide aptamer to levels comparable to that of an antibody (nanomolar range).

An antibody to a PD-L3 protein can be generated using methods that are well-known in the art. An anti-PD-L3 antibody is intended to include a polyclonal and monoclonal antibody; humanized antibody; murine antibody; mouse-human antibody; mouse-primate antibody; and chimeric antibody; wherein the antibody can be an intact molecule, a fragment thereof (such as scFv, Fv, Fd, Fab, Fab' or F(ab)'$_2$ fragment), or a multimer or aggregate of intact molecules and/or fragments; and can occur in nature or be produced, e.g., by immunization, synthesis or genetic engineering. An antibody fragment, as used herein, refers to fragments, derived from or related to an antibody, which bind antigen and which can be derivatized to exhibit structural features that facilitate clearance and uptake, e.g., by the incorporation of galactose residues. This includes, e.g., F(ab), F(ab)'$_2$, scFv, light chain variable region ($V_L$), heavy chain variable region ($V_H$), and combinations thereof.

Monoclonal antibodies to PD-L3 protein of the invention can be prepared using any technique which provides for the production of antibody molecules by continuous cell lines in culture. These include, but are not limited to, the hybridoma technique, the human B-cell hybridoma technique, and the EBV-hybridoma technique (Kohler, et al. (1975) *Nature* 256: 495-497; Kozbor, et al. (1985) *J. Immunol. Methods* 81:31-42; Cote, et al. (1983) *Proc. Natl. Acad. Sci.* 80:2026-2030; Cole, et al. (1984) *Mol. Cell. Biol.* 62:109-120).

In addition, techniques developed for the production of humanized and chimeric antibodies, the splicing of mouse antibody genes to human antibody genes to obtain a molecule with appropriate antigen specificity and biological activity, can be used (Morrison, et al. (1984) *Proc. Natl. Acad. Sci.* 81, 6851-6855; Neuberger, et al. (1984) *Nature* 312:604-608; Takeda, et al. (1985) *Nature* 314:452-454). Alternatively, techniques described for the production of single-chain antibodies can be adapted, using methods known in the art, to produce specific, single-chain antibodies. Antibodies with related specificity, but of distinct idiotypic composition, can be generated by chain shuffling from random combinatorial immunoglobulin libraries (Burton (1991) *Proc. Natl. Acad. Sci.* 88, 11120-11123).

Antibodies can also be produced by inducing in vivo production in the lymphocyte population or by screening immunoglobulin libraries or panels of highly specific binding reagents as is well-known in the art (Orlandi, et al. (1989) *Proc. Natl. Acad. Sci.* 86: 3833-3837; Winter, et al. (1991) *Nature* 349:293-299).

Diabodies are also contemplated. A diabody refers to an engineered antibody construct prepared by isolating the binding domains (both heavy and light chain) of a binding antibody, and supplying a linking moiety which joins or operably links the heavy and light chains on the same polypeptide chain thereby preserving the binding function (see, Holliger et al. (1993) *Proc. Natl. Acad. Sci. USA* 90:6444; Poljak (1994) *Structure* 2:1121-1123). This forms, in essence, a radically abbreviated antibody, having only the variable domain necessary for binding the antigen. By using a linker that is too short to allow pairing between the two domains on the same chain, the domains are forced to pair with the complementary domains of another chain and create two antigen-binding sites. These dimeric antibody fragments, or diabodies, are bivalent and bispecific. It should be clear that any method to generate diabodies, as for example described by Holliger, et al. (1993) supra, Poljak (1994) supra, Zhu, et al. (1996) *Biotechnology* 14:192-196, and U.S. Pat. No. 6,492,123, herein incorporated by reference, can be used. In one embodiment, an antibody or diabody of the present invention is a bispecific agonistic antibody which specifically agonizes CD3 and PD-L3-receptors and co-stimulates T cell activation.

Various immunoassays can be used for screening to identify antibodies, or fragments thereof, having the desired specificity for PD-L3 protein. Numerous protocols for competitive binding (e.g, ELISA), latex agglutination assays, immunoradiometric assays, and kinetics (e.g. BIACORE™ analysis) using either polyclonal or monoclonal antibodies, or fragments thereof, and are well-known in the art. Such immunoassays typically involve the measurement of complex formation between a specific antibody and its cognate antigen. A two-site, monoclonal-based immunoassay utilizing monoclonal antibodies reactive to two non-interfering epitopes is suitable, but a competitive binding assay can also be employed.

An antibody of the instant invention is useful producing a corresponding anti-idiotypic antibody. Anti-idiotypic antibodies, or anti-idiotypes are antibodies directed against the antigen-combining region or variable region (idiotype) of another antibody. Based on Jerne's network model of idiotypic relationships (Jerne (1974) *Ann. Immunol.* 125:373; Jerne, et al. (1982) *EMBO J.* 1:234), immunization with an antibody molecule expressing a paratope (antigen-combining site) for a given antigen produces a group of anti-antibodies, some of which share with the antigen a complementary structure to the paratope. Such anti-idiotypic antibodies would be useful for antagonizing or agonizing the PD-L3 receptor.

In one embodiment, an anti-PD-L3 antibody, or peptide aptamer, of the instant invention is agonistic which, like PD-L3 protein, binds a PD-L3 receptor and activates the receptor. In another embodiment, the anti-PD-L3 antibody, or peptide aptamer, is antagonistic and blocks the binding of PD-L3 protein to its cognate receptor on an immune cell thereby blocking activation of the receptor. Like a PD-L3 protein, such PD-L3 binding agents are useful in methods for modulating an immune cell response.

Also encompassed by the present invention are small molecules which can modulate (either enhance or inhibit) interactions between PD-L3 and its cognate receptor(s). Such small molecules can be obtained using any of the numerous approaches in combinatorial library methods known in the art, including spatially addressable parallel solid phase or solution phase libraries; synthetic library methods requiring deconvolution; the one-bead one-compound library method; and synthetic library methods using affinity chromatography selection. (Lam (1997) *Anticancer Drug Des.* 12:145).

Examples of methods for the synthesis of molecular libraries can be found in the art, for example in, DeWitt, et al. (1993) *Proc. Natl. Acad. Sci. USA* 90:6909; Erb, et al. (1994) *Proc. Natl. Acad. Sci. USA* 91:11422; Zuckermann, et al. (1994) *J. Med. Chem.* 37:2678; Cho, et al. (1993) *Science* 261:1303; Carrell, et al. (1994) Angew. Chem. Int. Ed. Engl. 33:2059; and Gallop, et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria or spores (U.S. Pat. No. 5,223,409), plasmids (Cull, et al. (1992) *Proc. Natl. Acad. Sci. USA* 89:1865-1869) or on phage (Scott and Smith (1990) *Science* 249:386-390; Devlin (1990) *Science* 249:404-406; Cwirla, et al. (1990) *Proc. Natl. Acad. Sci. USA* 87:6378-6382; Felici (1991) *J. Mol. Biol.* 222:301-310). Compounds can be screened in cell-based or non-cell-based assays. Compounds can be screened in pools (e.g., multiple compounds in each testing sample) or as individual compounds.

A small molecule for modulating interactions between PD-L3 and its cognate receptor can be identified, for example, in a cell-based assay. Such an assay involves contacting a cell expressing a PD-L3 receptor (e.g., a T cell), with a test molecule and determining the ability of the test molecule to modulate (e.g., stimulate or inhibit) the binding of PD-L3 to its binding partner. Determining the ability of the PD-L3 to bind to, or interact with, its binding partner can be accomplished, e.g., by measuring direct binding or by measuring a parameter of immune cell activation (e.g., cell proliferation or cytokine production). In a direct binding assay, the PD-L3 protein can be coupled with a radioisotope (e.g., $^{125}I$, $^{35}S$, $^{14}C$, or $^{3}H$) such that binding of PD-L3 can be determined by detecting the labeled protein in a complex (e.g., direct counting of radioemission or by scintillation counting). Alternatively, PD-L3 can be enzymatically labeled with, for example, horseradish peroxidase, alkaline phosphatase, or luciferase, and the enzymatic label detected by determination of conversion of an appropriate substrate to product.

In one embodiment, a small molecule binds to antagonizes the interaction between PD-L3 and at least one cognate receptor. in another embodiment, the small molecule agonizes the interaction between PD-L3 and at least one cognate receptor.

PD-L3 protein, PD-L3 binding agents (antagnostic or agonistic), small molecule agonists or antagonists, vectors, isolated host cells or T cells activated by the methods described herein can be used for modulating immune responses in subjects for treating and preventing cancer, infectious disease, autoimmune disease, immune dysfunction related to aging, transplantation or any other disease state where such agents are desired for treatment. Such modulatory agents (i.e., PD-L3 protein, PD-L3 binding agents, small molecule agonists or antagonists, vectors, isolated host cells or activated T cells) can be administered either alone, or as a pharmaceutical composition in combination with diluents and/or with other components such as cytokines or other cell populations (e.g., APCs). In general, a pharmaceutical composition containing a modulatory agent is formulated with one or more pharmaceutically acceptable carriers such as those described herein.

A modulatory agent described herein can be used in methods of prevention or treatment (e.g., by up- or down-modulating the immune response). Such methods involve administration to a subject, at risk of having or having a disease or condition associated with an unwanted or less than desirable immune response, a prophylactic or therapeutic agent prior to or after the manifestation of symptoms associated with an unwanted or less than desirable immune response. Subjects at risk or having a disease that would benefit from treatment with such agents or methods can be identified, for example, by any or a combination of diagnostic or prognostic assays known in the art. The appropriate agent used for treatment (e.g. antibodies, peptides, fusion proteins or small molecules) can be determined based on clinical indications and can be identified, e.g., using screening assays described herein. Modulatory agents can be administered in vitro (e.g., by contacting the cell with the agent) or, alternatively, in vivo (e.g., by administering the agent to a subject). As such, the present invention relates to methods of treating an individual afflicted with a disease or disorder that would benefit from modulation of an immune response, e.g., by modulation of the interaction between a PD-L3 ligand its cognate receptor(s). As PD-L3 expression was predominantly localized to the brain, one embodiment of the present invention is the prevention or treatment of a disease or condition of the brain.

To illustrate the efficacy of using a PD-L3 protein, co-stimulation (i.e., CD3/CD30-mediated) has been successfully used in in vivo tumor-specific activation of the T cell cytolytic machinery (see, Bauer, et al. (1999) *Cancer Res.* 59:1961-5). Likewise, CD3/CD28-activated T cells and interleukin-2 administration has achieved tumor regression in bone metastases in Phase I clinical trials of metastatic renal cell carcinoma (Thompson, et al. (*Clin. Cancer Res.* 2003 Sep. 1; 9 (10 Pt 1):3562-7). Accordingly, it is contemplated that co-stimulation with PD-L3 in combination with a primary signal (e.g., anti-CD3) will be useful for modulating cellular immune responses mediated by cytotoxic T cells, capable of killing tumor and infected cells, and helper T cell responses.

The invention is described in greater detail by the following non-limiting examples.

Example 1

Expression Profiling

To facilitate comparisons with established expression profiles of $T^{reg}$ cells, standard growth and activation conditions were employed (McHugh, et al. (2002) supra). Briefly, fresh isolated $T^{reg}$ cells (~96% positive) were inoculated at $10^6$/mL into complete RPMI medium supplemented with 10% fetal bovine serum and 100 units IL-2 in a 24-well plate precoated with anti-CD3 with or without anti-GITR (DTA-1) (Shimizu, et al. (2002) supra). The cells were cultured at 37° C. for 0 and 12 hours, RNA was purified and subsequently analyzed using an AFFYMETRIX® mouse genome A430 oligonucleotide array.

By comparing the data from resting or activated $CD4^+$ $CD25^+$ T cell groups, gene expression patterns were found to be similar to those established in the art (Gavin, et al. (2002) supra; McHugh, et al. (2002) supra). It identify genes regulated by GIRT signaling, gene expression profiles were compared between the different cell populations with or without anti-GITR treatment. A list of known as well as unknown genes were compiled including the previously uncharacterized PD-L3 and $T^{reg}$-sTNF.

Example 2

Inhibitory Activity of PD-L3

The inhibitory activity of PD-L1 was revealed by using antigen presenting cells over-expressing PD-L1 in vitro with $CD4^+$ and $CD8^+$ T cell antigen receptor transgenic T cells and antigen stimulation (Carter, et al. (2002) Eur. J. Immunol. 32:634-43). Similarly, the lentivector disclosed herein, which expresses the full-length PD-L3, is transduced into cell lines expressing class II major histocompatibility complex (MHC) and class I MHC. The response of TEa Tg or the 2C transgenic T cells to antigen presented by empty vector-transduced or PD-L3-transduced antigen presenting cells is determined according to established methods.

Example 3

Protein Expression

Expression patterns in lymphoid, monocyte and dendritic cell subsets, as well as non-hemoatopoietic tissues, is determined by RT-PCR and western blot analysis using standard protocols in combination with the rabbit αPD-L3 antibody disclosed herein.

Example 4

PD-L3 Transgenic Mice

Using Lentiviral infection of embryos, four transgenic mice ubiquitously expressing PD-L3 have been produced. These mice are expected to spontaneously develop autoimmunity and in vivo immune responses in the PD-L3 transgenic mice (i.e., humoral immune responses, T cell priming, etc.) are evaluated to assess systemic autoimmune disease development.

Example 5

PD-L3 Knock-Out Mice

PD-L3 is inactivated by homologous recombination. A BAC clone containing full-length PD-L3 sequence was purchased from INVITROGEN™ (Carlsbad, Calif.). A PD-L3 targeting vector was generated by inserting a 1.6 kb fragment located at the 5' side of the second exon of PD-L3 gene upstream the neomycin gene and the 5 kb fragment located at the 3° side of the third exon of PD-L3 gene downstream the neomycin gene. B6-derived embryonic stem (ES) cells are electroporated with PD-L3 targeting vector and recombined clones are selected. Selected clones are then injected into C57BL/6 blastocytes and the resulting chimeric male offspring are mated to FLP-deleter mice to remove the neomycin cassette. Transmission of the targeted allele in the offspring is determined by PCR from genomic DNA. The second and the third exon contain the PD-L3 domain, therefore, the resulting mice have only the inactivated form of the PD-L3 molecule.

The overall immune capacity of PD-L3 deficient mice is determined as with other $PD-L^{-/-}$ mice, including assessment of T cell responses to antigen, humoral immune responses, overt autoimmunity (Systemic Lupus Erythematosus, inflammatory bowel disease), and increased susceptibility to induced autoimmune disease (experimental autoimmune encephalomyelitis) (Chen (2004) supra).

What is claimed is:

1. A method of promoting T cell immunity against a viral infectious agent comprising administering an effective amount of an anti-PD-L3 antibody or antibody fragment that specifically binds to the extracellular region of the human PD-L3 protein having the sequence in SEQ ID NO:4, wherein said anti-PD-L3 antibody or antibody fragment antagonizes the immunosuppressive effect of PD-L3 on T cell immunity in vivo, and thereby potentiates T cell immune response against the viral infectious agent.

2. The method of claim 1, wherein the anti-PD-L3 antibody or antibody fragment antagonizes one or more of the following effects of PD-L3 on T cell function in vivo:
   (1) suppression of T cell activation or differentiation;
   (2) suppression of CD4+T cell proliferation,
   (3) suppression of CD8+T cell proliferation and
   (4) suppression of cytokine production by T cells.

3. The method of claim 1, wherein the antibody or antibody fragment is a chimeric, human or humanized antibody or fragment thereof.

4. The method of claim 1, wherein the antibody fragment is selected from a Fab, F(ab')2, Fv, Fd, and a scFv.

5. The method of claim 1, wherein the antibody is an IgG1.

6. The method of claim 1, which promotes T cell-mediated killing of virally infected cells.

* * * * *

SEQUENCE LISTING

```
<160> NUMBER OF SEQ ID NOS: 10

<210> SEQ ID NO 1
<211> LENGTH: 4795
<212> TYPE: DNA
<213> ORGANISM: Mus musculus

<400> SEQUENCE: 1
gagcattcac tctagcgagc gagcggcgtg tacagccggc tccctgggct cctggagtcc        60
cgcttgctcc aagcgcactc cagcagtctc tttctgctct tgcccggctc gacggcgaca       120
tgggtgtccc cgcggtccca gaggccagca gcccgcgctg gggaaccctg ctccttgcta       180
ttttcctggc tgcatccaga ggtctggtag cagccttcaa ggtcaccact ccatattctc       240
```

```
tctatgtgtg tcccgaggga cagaatgcca ccctcacctg caggattctg ggccccgtgt      300
ccaaagggca cgatgtgacc atctacaaga cgtggtacct cagctcacga ggcgaggtcc      360
agatgtgcaa agaacaccgg cccatacgca acttcacatt gcagcacctt cagcaccacg      420
gaagccacct gaaagccaac gccagccatg accagcccca gaagcatggg ctagagctag      480
cttctgacca ccacggtaac ttctctatca ccctgcgcaa tgtgacccca agggacagcg      540
gcctctactg ctgtctagtg atagaattaa aaaaccacca cccagaacaa cggttctacg      600
ggtccatgga gctacaggta caggcaggca aaggctcggg gtccacatgc atggcgtcta      660
atgagcagga cagtgacagc atcacggctg cggccctggc caccggcgcc tgcatcgtgg      720
gaatcctctg cctcccccTT atcctgctgc tggtctataa gcagagacag gtggcctctc      780
accgccgtgc ccaggagttg gtgaggatgg acagcagcaa cacccaagga atcgaaaacc      840
caggcttcga gaccactcca cccttccagg ggatgcctga ggccaagacc aggccgccac      900
tgtcctatgt ggcccagcgg caaccttcgg agtcaggacg gtacctgctc tctgaccccaa     960 gcacacctct gtcgcctcca ggccctgggg acgtcttttt cccatcccta gatccagtcc     1020
ctgactcccc taactctgaa gccatctaaa ccagctgggg aaccatgaac catggtacct     1080
gggtcaggga tatgtgcact tgatctatgg ctggcccttg acagtctttt taggcactga     1140
ctccagcttc cttgctcctg ctctgagcct agactctgct tttacaagat gcacagaccc     1200
tcccctatct ctttcagacg ctacttgggg ggcagggaga agatgttgga ttgctcattg     1260
ctgttctcaa gatcttggga tgctgagttc tccctagaga cttgacttcg acagccacag     1320
atgtcagatg acctgcatcc tatgaacgtc cggcttggca agagcctttc ttcatggaaa     1380
ccagtagccc ggaggggatg aggtaggcac cttgccaccc tcccgggaga gagacacaag     1440
atgtgagaga ctcctgctca ctgtgggggt gtggctggcc tgcttgtttg cctgaggatg     1500
ctcctctgtt ggactgactc tatcccctg gattctggag cttggctggc ctatgtccca     1560
ccagaggagc atctcagcag ccttccacca gcaacctgag ggcctgccag cttcgtggct     1620
ctgggctctc attacctgta tggccgtcca cagagctcag tggccagagg ctttgaaaca     1680
ggaagtacat gtcaggttca ggaaccactg tgagctcatt agtgtcttga gcaatgtgag     1740
gcctggacca gtggacacgg agggaggggtg gcgagaggat gatggggatg atgaggggaa     1800
cacgctccct tcctgtcctt gtcatccacc actaccacta ttcagtgtgg agcagtggca     1860
aaggtgaccg acctccacaa tgtcctagtg atgctggacc atttctaagt gtgaaagaga     1920
tgctattaaa aacagtatgt ggcaatggct gccaacagct gagtggactg gaggcactgg     1980
ctttaaggcc ctggaggtgc agggcccggt atggggatag gatgggagt ttcagtgagg     2040 gcctagggat cactccgctt ctgaccactc ttcttctgag cctcacctca gggtgacctt     2100
caggcacaca gaaagagcttg cccctggtcc gatactactc ttggctctca tctccagggt     2160
ttggcatgac ctgggcacac aggggggagtc ttcagaaagg attttaaagc atgaaaagaa     2220
agggtagttc ttgtgaggta gggatgggca gctgatgttt gagagtgagg agggatacgg     2280
ctgggcagat cactctccag tctctagagg gaaagtagct ctaagtctgg gagagcagca     2340
gcccagtggt accatatgtc ttcttgcagc ttccactggc tgggctgaac tgggcatggg     2400
taggaaagct cctgttctgg gcctgcagcc agggagaacc ccattcattc cctgaggaca     2460
gatgggtggg gagagaagag agagtttcag gccgggaagc agcaataagc tatctgctgg     2520
ggacccagac aagttgtctg atgaggtcca agatgtggga tgccagttat acctgggggct    2580 tggggatcct tagaggcttt gtatcatcat cataggagtg tcggggtggc cagggcatca    2640
```

```
aagccatgac ccctgtttta tcctcagggt ccactcttct gcaccatcca ttgctctaga   2700
tctatgcagt tactatagac agaatgtgtt gttctgtttg ctttggggga taatggcctg   2760
gcgaactgcc agctgttcag tggcagggct gtgaggccag tcaaagacta gaacccacag   2820
accagctgaa cgatgagtat agcctgtccc ctggggagc ctgacctgtc tccagccta    2880 agcttcagac ctcaccactc agatgacttc taagaatttg cctgtgggga ccctgcatg    2940 gctgcagctc cgtggaaagg agaggaggcc cccagcagaa gaaccactcg cttcctgccc   3000
agcttcctcc tgtagggctc taagtctctt cttcttggga ccctgcaagc aaaggcatgt   3060
cagcttggtg gtttcctgtt ttgggtgaag ttttgtgtgg tccgggttct gtctacatcc   3120
atgaacttgg ggtgctacca ccttgctgct gctgtagaga cagctgcagg atcttagggt   3180
ggaaaatgga ggtgccctga ggtgctagcc cttggggcaa agatggggt ggcaatgaga    3240 cacagtgggg aactgagttc cccaagagga gggaggagcc ctgtagcctc aagggccata   3300
ttgggttcct ggtaccagca aaagcctaga gagcgaagtc tgtattttga ggaggtaatt   3360
gatccttacg gaatccatca gaaatttgga gcgggtgctt tatctatctc tggagggtct   3420
ctacctatct ccgatgaagc tctccctggg cctgggatgg gagaaaccag gaggaaaggt   3480
gtctgataaa gcaggggctt cttgacaagc caaagggcca ctggtagctg ttgtggaccg   3540
agctgaccct gctgaagtat tgtagtgtgc cttggaccaa cttctcaaaa gagcaacccc   3600
ggggctaccc tacttctgcc aggaagaggc ggagaagggg ctgagaggcc tggaagggc    3660 tagctccttc tttgagaact gctccccgga ggacttggag gaggcggcta ggctacgggc   3720
tgctgagggc cctttgtctt tcctaacctg ggcactgtta ggatgctccc tcctggaaaa   3780
ggctttcctg ggtgtgagct agagcagtgt ccatgccagc gctgaacctg ccatggtggg   3840
agctgaacta aaaatttctc agggaactaa aataggcaaa gaggaactg ggggaggagg    3900 gtgccaggca ggatggggg aagggagggc agtgcaaaag tctcttgaaa cacagacagc    3960
ccagctgagt gccagtccca gatcacagag aatacggctc atctggctca tgttctgcat   4020
gcttgctgct ttaccctggc actttccttc tccaccatga gtgcgagtcc tgggagtcct   4080
gggagggtga ggattaatgc cagcctgggg agcagatagc tgacagagtc cttgggtaac   4140
tggcttgaac caggacctca ggattccact ctggggatct agctttgtct gggccagtga   4200
agatctctat aatggcatta ttgccagggg ataaacattt cactgggttc tgatctgttg   4260
ggtgtggctt cctggaaaat atggtgagag gaattctgct aaggatacag ttgataagaa   4320
agttctgaga ttgattagta atgcctgcct tggactcagg aagggaagtg gcagtatgaa   4380
tgccatgtct taatcatttt ggttaaaata tgcttcccaa aagatttcca cgtgtgttct   4440
tgtttatttg acatctgtct ccatatcagt cttgaaagcc tttctgtgtg tatatatatg   4500
atgtttgcgt gtatatatgt ttttgtgtgt gcatatggaa gtcagaaatc actgggtgtc   4560
ttcctccatt cctttgcaat gtatgttttt ttttttttta cgatttattt actatatgaa   4620
tgttttgcct gaatacatgc ataggtgtca cgtacatgcc tgctgaacg cttgaactg     4680 gagttacagg tggctatgag ctacagtgtg agcactggga atcaaacctg ggtcttctgc   4740
aagagcaaca aattaaaagt cagctcttaa ctacttgagc tattttccca actcc        4795
```

<210> SEQ ID NO 2
<211> LENGTH: 309
<212> TYPE: PRT
<213> ORGANISM: Mus musculus

<400> SEQUENCE: 2

Met Gly Val Pro Ala Val Pro Glu Ala Ser Ser Pro Arg Trp Gly Thr
1               5                   10                  15

Leu Leu Leu Ala Ile Phe Leu Ala Ala Ser Arg Gly Leu Val Ala Ala
            20                  25                  30

Phe Lys Val Thr Thr Pro Tyr Ser Leu Tyr Val Cys Pro Glu Gly Gln
        35                  40                  45

Asn Ala Thr Leu Thr Cys Arg Ile Leu Gly Pro Val Ser Lys Gly His
    50                  55                  60

Asp Val Thr Ile Tyr Lys Thr Trp Tyr Leu Ser Ser Arg Gly Glu Val
65                  70                  75                  80

Gln Met Cys Lys Glu His Arg Pro Ile Arg Asn Phe Thr Leu Gln His
                85                  90                  95

Leu Gln His His Gly Ser His Leu Lys Ala Asn Ala Ser His Asp Gln
                100                 105                 110

Pro Gln Lys His Gly Leu Glu Leu Ala Ser Asp His His Gly Asn Phe
            115                 120                 125

Ser Ile Thr Leu Arg Asn Val Thr Pro Arg Asp Ser Gly Leu Tyr Cys
        130                 135                 140

Cys Leu Val Ile Glu Leu Lys Asn His His Pro Glu Gln Arg Phe Tyr
145                 150                 155                 160

Gly Ser Met Glu Leu Gln Val Gln Ala Gly Lys Gly Ser Gly Ser Thr
                165                 170                 175

Cys Met Ala Ser Asn Glu Gln Asp Ser Asp Ser Ile Thr Ala Ala Ala
                180                 185                 190

Leu Ala Thr Gly Ala Cys Ile Val Gly Ile Leu Cys Leu Pro Leu Ile
            195                 200                 205

Leu Leu Leu Val Tyr Lys Gln Arg Gln Val Ala Ser His Arg Arg Ala
        210                 215                 220

Gln Glu Leu Val Arg Met Asp Ser Ser Asn Thr Gln Gly Ile Glu Asn
225                 230                 235                 240

Pro Gly Phe Glu Thr Thr Pro Pro Phe Gln Gly Met Pro Glu Ala Lys
                245                 250                 255

Thr Arg Pro Pro Leu Ser Tyr Val Ala Gln Arg Gln Pro Ser Glu Ser
                260                 265                 270

Gly Arg Tyr Leu Leu Ser Asp Pro Ser Thr Pro Leu Ser Pro Pro Gly
            275                 280                 285

Pro Gly Asp Val Phe Phe Pro Ser Leu Asp Pro Val Pro Asp Ser Pro
        290                 295                 300

Asn Ser Glu Ala Ile
305

<210> SEQ ID NO 3
<211> LENGTH: 4774
<212> TYPE: DNA
<213> ORGANISM: Homo sapiens

<400> SEQUENCE: 3
gggggcgggt gcctggagca cggcgctggg gccgcccgca cgctcactc gctcgcactc      60 agtcgcggga ggcttcccg cgccggccgc gtcccgcccg ctccccggca ccagaagttc     120
ctctgcgcgt ccgacggcga catgggcgtc cccacggccc tggaggccgg cagctggcgc    180
tggggatccc tgctcttcgc tctcttcctg gctgcgtccc taggtccggt ggcagccttc    240
aaggtcgcca cgccgtattc cctgtatgtc tgtcccgagg ggcagaacgt caccctcacc    300
tgcaggctct gggccctgt ggacaaaggg cacgatgtga ccttctacaa gacgtggtac    360

```
cgcagctcga ggggcgaggt gcagacctgc tcagagcgcc ggcccatccg caacctcacg      420
ttccaggacc ttcacctgca ccatggaggc caccaggctg ccaacaccag ccacgacctg      480
gctcagcgcc acgggctgga gtcggcctcc gaccaccatg gcaacttctc catcaccatg      540
cgcaacctga ccctgctgga tagcggcctc tactgctgcc tggtggtgga gatcaggcac      600
caccactcgg agcacagggt ccatggtgcc atggagctgc aggtgcagac aggcaaagat      660
gcaccatcca actgtgtggt gtacccatcc tcctcccagg atagtgaaaa catcacggct      720
gcagccctgg ctacgggtgc ctgcatcgta ggaatcctct gcctcccct catcctgctc       780 ctggtctaca agcaaaggca ggcagcctcc aaccgccgtg cccaggagct ggtgcggatg      840
gacagcaaca ttcaagggat tgaaaacccc ggctttgaag cctcaccacc tgcccagggg      900
atacccgagg ccaaagtcag gcacccctg tcctatgtgg cccagcggca gccttctgag       960
tctgggcggc atctgctttc ggagcccagc accccctgt ctcctccagg ccccggagac      1020
gtcttcttcc catccctgga ccctgtccct gactctccaa actttgaggt catctagccc     1080 agctgggga cagtgggctg ttgtggctgg gtctggggca ggtgcatttg agccagggct      1140
ggctctgtga gtggcctcct tggcctcggc cctggttccc tccctcctgc tctgggctca     1200
gatactgtga catcccagaa gcccagcccc tcaacccctc tggatgctac atggggatgc     1260
tggacggctc agcccctgtt ccaaggattt tggggtgctg agattctccc ctagagacct     1320
gaaattcacc agctacagat gccaaatgac ttacatctta agaagtctca gaacgtccag     1380
cccttcagca gctctcgttc tgagacatga gccttgggat gtggcagcat cagtgggaca     1440
agatggacac tgggccaccc tcccaggcac cagacacagg gcacggtgga gagacttctc     1500
ccccgtggcc gccttggctc cccgttttg cccgaggctc tcttctgtc agacttcctc       1560 tttgtaccac agtggctctg ggccaggcc tgcctgccca ctggccatcg ccaccttccc      1620
cagctgcctc ctaccagcag tttctctgaa gatctgtcaa caggttaagt caatctgggg     1680
cttccactgc ctgcattcca gtccccagag cttggtggtc ccgaaacggg aagtacatat     1740
tggggcatgg tggcctccgt gagcaaatgg tgtcttgggc aatctgaggc caggacagat     1800
gttgccccac ccactggaga tggtgctgag ggaggtgggt ggggccttct gggaaggtga     1860
gtggagaggg gcacctgccc cccgcccctcc ccatccccta ctcccactgc tcagcgcggg    1920
ccattgcaag ggtgccacac aatgtcttgt ccaccctggg acacttctga gtatgaagcg     1980
ggatgctatt aaaaactaca tgggaaaca ggtgcaaacc ctggagatgg attgtaagag      2040
ccagtttaaa tctgcactct gctgctcctc ccccaccccc accttccact ccatacaatc     2100
tgggcctggt ggagtcttcg cttcagagcc attcggccag gtgcgggtga tgttcccatc     2160
tcctgcttgt gggcatgccc tggctttgtt tttatacaca taggcaaggt gagtcctctg     2220
tggaattgtg attgaaggat tttaaagcag gggaggagag tagggggcat ctctgtacac     2280
tctgggggta aaacagggaa ggcagtgcct gagcatgggg acaggtgagg tggggctggg     2340 cagacccct gtagcgttta gcaggatggg ggccccaggt actgtggaga gcatagtcca     2400
gcctgggcat ttgtctccta gcagcctaca ctggctctgc tgagctgggc ctgggtgctg     2460
aaagccagga tttggggcta ggcgggaaga tgttcgccca attgcttggg gggttggggg     2520
gatggaaaag gggagcacct ctaggctgcc tggcagcagt gagccctggg cctgtggcta     2580
cagccaggga accccacctg gacacatggc cctgcttcta agccccccag ttaggcccaa     2640
aggaatggtc cactgagggc ctcctgctct gcctgggctg ggcagggc tttgaggaga       2700 gggtaaacat aggcccggag atggggctga cacctcgagt ggccagaata tgcccaaacc     2760
```

```
ccggcttctc ccttgtccct aggcagaggg gggtcccttc ttttgttccc tctggtcacc    2820
acaatgcttg atgccagctg ccataggaag agggtgctgg ctggccatgg tgcacacac    2880 ctgtcctccc agcactttgc agggctgagg tggaaggacc gcttaagccc aggtgttcaa    2940
ggctgctgtg agctgtgttc gagccactac actccagcct ggggacggag caaaactttg    3000
cctcaaaaca aattttaaaa agaaagaaag aaggaaagag ggtatgtttt tcacaattca    3060
tgggggcctg catggcagga gtggggacag gacacctgct gttcctggag tcgaaggaca    3120
agcccacagc ccagattccg gttctcccaa ctcaggaaga gcatgccctg ccctctgggg    3180
aggctggcct ggccccagcc ctcagctgct gaccttgagg cagagacaac ttctaagaat    3240
ttggctgcca gacccaggc ctggctgctg ctgtgtggag agggaggcgg cccgcagcag    3300
aacagccacc gcacttcctc ctcagcttcc tctggtgcgg ccctgccctc tcttctctgg    3360
acccttttac aactgaacgc atctgggctt cgtggtttcc tgttttcagc gaaatttact    3420
ctgagctccc agttccatct tcatccatgg ccacaggccc tgcctacaac gcactaggga    3480
cgtccctccc tgctgctgct ggggaggggc aggctgctgg agccgccctc tgagttgccc    3540
gggatggtag tgcctctgat gccagccctg gtggctgtgg gctggggtgc atgggagagc    3600
tgggtgcgag aacatggcgc ctccaggggg cgggaggagc actaggggct ggggcaggag    3660
gctcctggag cgctggattc gtggcacagt ctgaggccct gagagggaaa tccatgcttt    3720
taagaactaa ttcattgtta ggagatcaat caggaattag gggccatctt acctatctcc    3780
tgacattcac agtttaatag agacttcctg cctttattcc ctcccaggga gaggctgaag    3840
gaatggaatt gaaagcacca tttggagggt tttgctgaca cagcggggac tgctcagcac    3900
tccctaaaaa cacaccatgg aggccactgg tgactgctgg tgggcaggct ggccctgcct    3960 ggggagtcc gtggcgatgg gcgctggggt ggaggtgcag gagccccagg acctgctttt    4020
caaaagactt ctgcctgacc agagctccca ctacatgcag tggcccaggg cagaggggct    4080
gatacatggc cttttcagg gggtgctcct cgcggggtgg acttgggagt gtgcagtggg    4140 acaggggct gcaggggtcc tgccaccacc gagcaccaac ttggcccctg ggtcctgcc    4200 tcatgaatga ggccttcccc agggctggcc tgactgtgct gggggctggg ttaacgtttt    4260
ctcagggaac cacaatgcac gaaagaggaa ctggggttgc taaccaggat gctgggaaca    4320
aaggcctctt gaagcccagc cacagcccag ctgagcatga gcccagccc atagacggca    4380 caggccacct ggcccattcc ctgggcattc cctgctttgc attgctgctt ctcttcaccc    4440
catggaggct atgtcaccct aactatcctg gaatgtgttg agagggattc tgaatgatca    4500
atatagcttg gtgagacagt gccgagatag atagccatgt ctgccttggg cacgggagag    4560
ggaagtggca gcatgcatgc tgtttcttgg cctttctgt tagaatactt ggtgctttcc    4620
aacacacttt cacatgtgtt gtaacttgtt tgatccaccc ccttccctga aaatcctggg    4680
aggttttatt gctgccattt aacacagagg gcaatagagg ttctgaaagg tctgtgtctt    4740
gtcaaaacaa gtaaacggtg gaactacgac taaa                                4774
```

<210> SEQ ID NO 4
<211> LENGTH: 311
<212> TYPE: PRT
<213> ORGANISM: Homo sapiens

<400> SEQUENCE: 4

```
Met Gly Val Pro Thr Ala Leu Glu Ala Gly Ser Trp Arg Trp Gly Ser
1               5                   10                  15
```

```
Leu Leu Phe Ala Leu Phe Leu Ala Ala Ser Leu Gly Pro Val Ala Ala
             20                  25                  30

Phe Lys Val Ala Thr Pro Tyr Ser Leu Tyr Val Cys Pro Glu Gly Gln
             35                  40                  45

Asn Val Thr Leu Thr Cys Arg Leu Leu Gly Pro Val Asp Lys Gly His
 50                  55                  60

Asp Val Thr Phe Tyr Lys Thr Trp Tyr Arg Ser Ser Arg Gly Glu Val
 65                  70                  75                  80

Gln Thr Cys Ser Glu Arg Arg Pro Ile Arg Asn Leu Thr Phe Gln Asp
             85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
            115                 120                 125

Phe Ser Ile Thr Met Arg Asn Leu Thr Leu Leu Asp Ser Gly Leu Tyr
            130                 135                 140

Cys Cys Leu Val Val Glu Ile Arg His His Ser Glu His Arg Val
145                 150                 155                 160

His Gly Ala Met Glu Leu Gln Val Gln Thr Gly Lys Asp Ala Pro Ser
            165                 170                 175

Asn Cys Val Val Tyr Pro Ser Ser Ser Gln Asp Ser Glu Asn Ile Thr
            180                 185                 190

Ala Ala Ala Leu Ala Thr Gly Ala Cys Ile Val Gly Ile Leu Cys Leu
            195                 200                 205

Pro Leu Ile Leu Leu Leu Val Tyr Lys Gln Arg Gln Ala Ala Ser Asn
210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
            245                 250                 255

Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
            275                 280                 285

Pro Gly Pro Gly Asp Val Phe Phe Pro Ser Leu Asp Pro Val Pro Asp
290                 295                 300

Ser Pro Asn Phe Glu Val Ile
305                 310

<210> SEQ ID NO 5
<211> LENGTH: 30
<212> TYPE: PRT
<213> ORGANISM: Artificial Sequence
<220> FEATURE:
<223> OTHER INFORMATION: Consensus sequence for PD-L3

<400> SEQUENCE: 5

Ile Thr Ala Ala Ala Leu Ala Thr Gly Ala Cys Ile Val Gly Ile Leu
 1               5                  10                  15

Cys Leu Pro Leu Ile Leu Leu Val Tyr Lys Gln Arg Gln
             20                  25                  30

<210> SEQ ID NO 6
<211> LENGTH: 1316
<212> TYPE: DNA
<213> ORGANISM: Mus musculus

<400> SEQUENCE: 6
```

```
ggagtcctcc ccttggagcc tgggaggcct agggagaaag tagttctctt tcggtggcag      60
ggttgctgtc gagggcaccg agcaggagga taggtcgaca gagacgagga gttctggctc     120
ctcctgcaga catgcaccag cggctgctgg gctcgtccct gggcctcgcc ccgcgcggg      180
ggctctgaat gcctgccgcc gccccatgaa gagcaccggc ctgggctccc gcccctaagc    240
ctctgctcgc ggagactgag ccatgtgggc ctggggctgg gccgctgcag cgctcctctg    300
gctacagact gcaggagccg gggcccggca ggagctcaag aagtctcggc agctgtttgc    360
gcgtgtggat ccccccaata ttaccacgtc caaccgtgag ggattcccag gctccgtcaa    420
gcccccggaa gcctctggac ctgagctctc agatgcccac atgacgtggt tgaactttgt    480
ccgacggcca gatgatgggt cctctagaaa acggtgtcgt ggccgggaca agaagtcgcg    540
aggcctctca ggtctcccag gccccccagg acctcctggc cctcctggtc ccctggctc    600
ccctggtgtg ggcgttaccc cagaggcctt actgcaggaa tttcaggaga tactgaaaga    660
ggccacagaa cttcgattct cagggctacc agacacattg ttaccccagg aacccagcca    720
acggctggtg gttgaggcct tctactgccg tttgaaaggc cctgtgctgg tggacaagaa    780
gactctggtg gaactgcaag gattccaagc tcctactact cagggcgcct tcctgcgggg    840
atctggcctg agcctgtcct tgggccgatt cacagcccca gtctctgcca tcttccagtt    900
ttctgccagc ctgcacgtgg accacagtga actgcagggc agaggccggt tgcgtacccg    960
ggatatggtc cgtgttctca tctgtattga gtccttgtgt catcgtcata cgtccctgga   1020
ggctgtatca ggtctggaga gcaacagcag ggtcttcaca gtgcaggttc agggggctgct  1080
gcatctacag tctggacagt atgtctctgt gttcgtggac aacagttctg ggcagtcct    1140
caccatccag aacacttcca gcttctcggg aatgcttttg ggtacctagc ggagctgaag  1200
aaacgattgt ggattgagga accaacacct tgcttcttag aggagctgaa aaggactact  1260
cactcccctt ttaatagttt tcatagcaat aaagaactcc aaacttcttc atcgct      1316
```

<210> SEQ ID NO 7
<211> LENGTH: 308
<212> TYPE: PRT
<213> ORGANISM: Mus musculus

<400> SEQUENCE: 7

```
Met Trp Ala Trp Gly Trp Ala Ala Ala Leu Leu Trp Leu Gln Thr
  1               5                  10                  15

Ala Gly Ala Gly Ala Arg Gln Glu Leu Lys Lys Ser Arg Gln Leu Phe
             20                  25                  30

Ala Arg Val Asp Ser Pro Asn Ile Thr Thr Ser Asn Arg Glu Gly Phe
         35                  40                  45

Pro Gly Ser Val Lys Pro Pro Glu Ala Ser Gly Pro Glu Leu Ser Asp
     50                  55                  60

Ala His Met Thr Trp Leu Asn Phe Val Arg Arg Pro Asp Asp Gly Ser
 65                  70                  75                  80

Ser Arg Lys Arg Cys Arg Gly Arg Asp Lys Lys Ser Arg Gly Leu Ser
                 85                  90                  95

Gly Leu Pro Gly Pro Pro Gly Pro Pro Gly Pro Pro Gly Pro Pro Gly
            100                 105                 110

Ser Pro Gly Val Gly Val Thr Pro Glu Ala Leu Leu Gln Glu Phe Gln
        115                 120                 125

Glu Ile Leu Lys Glu Ala Thr Glu Leu Arg Phe Ser Gly Leu Pro Asp
    130                 135                 140
```

Thr Leu Leu Pro Gln Glu Pro Ser Gln Arg Leu Val Val Glu Ala Phe
145                 150                 155                 160

Tyr Cys Arg Leu Lys Gly Pro Val Leu Val Asp Lys Lys Thr Leu Val
            165                 170                 175

Glu Leu Gln Gly Phe Gln Ala Pro Thr Thr Gln Gly Ala Phe Leu Arg
        180                 185                 190

Gly Ser Gly Leu Ser Leu Ser Leu Gly Arg Phe Thr Ala Pro Val Ser
            195                 200                 205

Ala Ile Phe Gln Phe Ser Ala Ser Leu His Val Asp His Ser Glu Leu
        210                 215                 220

Gln Gly Arg Gly Arg Leu Arg Thr Arg Asp Met Val Arg Val Leu Ile
225                 230                 235                 240

Cys Ile Glu Ser Leu Cys His Arg His Thr Ser Leu Glu Ala Val Ser
            245                 250                 255

Gly Leu Glu Ser Asn Ser Arg Val Phe Thr Val Gln Val Gln Gly Leu
        260                 265                 270

Leu His Leu Gln Ser Gly Gln Tyr Val Ser Val Phe Val Asp Asn Ser
        275                 280                 285

Ser Gly Ala Val Leu Thr Ile Gln Asn Thr Ser Ser Phe Ser Gly Met
        290                 295                 300

Leu Leu Gly Thr
305

<210> SEQ ID NO 8
<211> LENGTH: 1055
<212> TYPE: DNA
<213> ORGANISM: Homo sapiens

<400> SEQUENCE: 8
ctcgccgcgc tgagccgcct cgggacggag ccatgcggcg ctgggcctgg gccgcggtcg      60
tggtcctcct cgggccgcag ctcgtgctcc tcggggcgt cggggcccgg cgggaggcac     120
agaggacgca gcagcctggc cagcgcgcag atcccccccaa cgccaccgcc agcgcgtcct     180
cccgcgaggg gctgccccgag gccccaagc catcccaggc ctcaggacct gagttctccg     240
acgcccacat gacatggctg aactttgtcc ggcggccgga cgacggcgcc ttaaggaagc     300
ggtgcggaag cagggacaag aagccgcggg atctcttcgg tcccccagga cctccaggtg     360
cagaagtgac cgcggagact ctgcttcacg agtttcagga gctgctgaaa gaggccacgg     420
agcgccggtt ctcagggctt ctggacccgc tgctgcccca gggggcgggc ctgcggctgg     480
tgggcgaggc ctttcactgc cggctgcagg gtccccgccg ggtggacaag cggacgctgg     540
tggagctgca tggtttccag gctcctgctg cccaaggtgc cttcctgcga ggctccggtc     600
tgagcctggc ctcgggtcgg ttcacggccc ccgtgtccgg catcttccag ttctctgcca     660
gtctgcacgt ggaccacagt gagctgcagg gcaaggcccg gctgcgggcc cgggacgtgg     720
tgtgtgttct catctgtatt gagtccctgt gccagcgcca cacgtgcctg gaggccgtct     780
caggcctgga gagcaacagc agggtcttca cgctacaggt gcaggggctg ctgcagctgc     840
aggctggaca gtacgcttct gtgtttgtgg acaatggctc cggggccgtc ctcaccatcc     900
aggcgggctc cagcttctcc gggctgctcc tgggcacgtg agggcgccca gggggctgg     960 cgaggagctg ccgccggatc ccggggaccc tcctactgat gcccgtggtc accacaataa    1020
agagccctcc accctcaaaa aaaaaaaaaa aaaaa                                1055

<210> SEQ ID NO 9
<211> LENGTH: 302

```
<212> TYPE: PRT
<213> ORGANISM: Homo sapiens

<400> SEQUENCE: 9

Met Arg Arg Trp Ala Trp Ala Ala Val Val Leu Leu Gly Pro Gln
1               5                   10                  15

Leu Val Leu Leu Gly Gly Val Gly Ala Arg Arg Glu Ala Gln Arg Thr
            20                  25                  30

Gln Gln Pro Gly Gln Arg Ala Asp Pro Pro Asn Ala Thr Ala Ser Ala
            35                  40                  45

Ser Ser Arg Glu Gly Leu Pro Glu Ala Pro Lys Pro Ser Gln Ala Ser
    50                  55                  60

Gly Pro Glu Phe Ser Asp Ala His Met Thr Trp Leu Asn Phe Val Arg
65              70                  75                  80

Arg Pro Asp Asp Gly Ala Leu Arg Lys Arg Cys Gly Ser Arg Asp Lys
                85                  90                  95

Lys Pro Arg Asp Leu Phe Gly Pro Pro Gly Pro Pro Gly Ala Glu Val
            100                 105                 110

Thr Ala Glu Thr Leu Leu His Glu Phe Gln Glu Leu Leu Lys Glu Ala
            115                 120                 125

Thr Glu Arg Arg Phe Ser Gly Leu Leu Asp Pro Leu Leu Pro Gln Gly
    130                 135                 140

Ala Gly Leu Arg Leu Val Gly Glu Ala Phe His Cys Arg Leu Gln Gly
145                 150                 155                 160

Pro Arg Arg Val Asp Lys Arg Thr Leu Val Glu Leu His Gly Phe Gln
                165                 170                 175

Ala Pro Ala Ala Gln Gly Ala Phe Leu Arg Gly Ser Gly Leu Ser Leu
            180                 185                 190

Ala Ser Gly Arg Phe Thr Ala Pro Val Ser Gly Ile Phe Gln Phe Ser
    195                 200                 205

Ala Ser Leu His Val Asp His Ser Glu Leu Gln Gly Lys Ala Arg Leu
210                 215                 220

Arg Ala Arg Asp Val Val Cys Val Leu Ile Cys Ile Glu Ser Leu Cys
225                 230                 235                 240

Gln Arg His Thr Cys Leu Glu Ala Val Ser Gly Leu Glu Ser Asn Ser
                245                 250                 255

Arg Val Phe Thr Leu Gln Val Gln Gly Leu Leu Gln Leu Gln Ala Gly
            260                 265                 270

Gln Tyr Ala Ser Val Phe Val Asp Asn Gly Ser Gly Ala Val Leu Thr
    275                 280                 285

Ile Gln Ala Gly Ser Ser Phe Ser Gly Leu Leu Leu Gly Thr
    290                 295                 300

<210> SEQ ID NO 10
<211> LENGTH: 17
<212> TYPE: PRT
<213> ORGANISM: Artificial Sequence
<220> FEATURE:
<223> OTHER INFORMATION: Consensus sequence for Treg-sTNF

<400> SEQUENCE: 10

Ile Phe Gln Phe Ser Ala Ser Leu His Val Asp His Ser Glu Leu Gln
1               5                   10                  15

Gly
```